US007353827B2

(12) United States Patent
Geist (10) Patent No.: US 7,353,827 B2
(45) Date of Patent: Apr. 8, 2008

(54) MASK, MASK SHELL AND SEAL WITH IMPROVED MOUNTING, MASK SEAL, METHOD OF MASK MANUFACTURE AND MASK WITH REDUCED EXHALATION NOISE (75) Inventor: Leroy D. Geist, Parker, CO (US)

(73) Assignee: Vitol Signs, Inc., Totowa, NJ (US)

( * ) Notice: Subject to any disclaimer, the term of this patent is extended or adjusted under 35 U.S.C. 154(b) by 630 days.

(21) Appl. No.: 10/932,849

(22) Filed: Sep. 1, 2004

(65) Prior Publication Data

US 2006/0042629 A1    Mar. 2, 2006

(51) Int. Cl.
*A62B 18/08* (2006.01)
*A62B 18/02* (2006.01)

(52) U.S. Cl. .............................. 128/207.11; 128/206.21; 128/206.24

(58) Field of Classification Search ........... 128/202.27, 128/207.11, 207.13, 206.21, 206.23–28
See application file for complete search history.

(56) References Cited

U.S. PATENT DOCUMENTS

| | | | | |
|---|---|---|---|---|
| 5,647,357 | A | | 7/1997 | Barnett et al. ......... 128/206.24 |
| 5,880,232 | A | * | 3/1999 | Fujita et al. ................. 526/205 |
| 5,884,624 | A | | 3/1999 | Barnett et al. ......... 128/206.24 |
| 5,921,239 | A | * | 7/1999 | McCall et al. .......... 128/205.25 |
| 5,952,423 | A | * | 9/1999 | Shang et al. ................... 525/64 |
| 6,019,101 | A | | 2/2000 | Cotner et al. .......... 128/207.13 |
| 6,112,746 | A | | 9/2000 | Kwok et al. ............ 128/207.13 |
| 6,306,191 | B1 | * | 10/2001 | McInerney et al. ........ 55/385.4 |
| 6,357,441 | B1 | | 3/2002 | Kwok et al. ............ 128/207.13 |
| 6,374,826 | B1 | | 4/2002 | Gunaratnam et al. .. 128/206.27 |
| 6,397,847 | B1 | | 6/2002 | Scarberry et al. ...... 128/206.24 |
| 6,412,487 | B1 | | 7/2002 | Gunaratnam et al. .. 128/206.24 |
| 6,435,181 | B1 | * | 8/2002 | Jones et al. ............. 128/204.18 |
| 6,615,832 | B1 | * | 9/2003 | Chen ...................... 128/206.26 |
| 6,631,718 | B1 | | 10/2003 | Lovell .................... 128/206.24 |
| 6,634,358 | B2 | | 10/2003 | Kwok et al. ............ 128/205.25 |
| 6,668,830 | B1 | | 12/2003 | Hansen et al. ......... 128/206.21 |
| 6,694,973 | B1 | * | 2/2004 | Dunhao et al. ........ 128/203.12 |
| 6,817,362 | B2 | * | 11/2004 | Gelinas et al. ......... 128/206.17 |
| 6,823,869 | B2 | * | 11/2004 | Raje et al. .............. 128/206.24 |
| 7,159,587 | B2 | * | 1/2007 | Drew et al. ............. 128/204.18 |
| 2005/0103782 | A1 | * | 5/2005 | O'Brien et al. ............. 220/4.24 |
| 2006/0107960 | A1 | * | 5/2006 | Smart ..................... 128/206.24 |

FOREIGN PATENT DOCUMENTS

WO    WO 00/74758    12/2000
WO    WO 00/74958    12/2000

OTHER PUBLICATIONS

Mask Assembly, IQ Nasal Mask, SleepNetCorp, Monchester, NH, Author & Date Unknown 1 page SleepNet, IQ Nasal Mask Fitting Tips, 3-Point Strap, SleepNetCorp Monchester, NH, Author, Date Unknown.

* cited by examiner

*Primary Examiner*—Justine R. Yu
*Assistant Examiner*—Kristen C. Matter
(74) *Attorney, Agent, or Firm*—R. Gale Rhodes, Jr.

(57) ABSTRACT

Mask seal having an embedded mounting member for engaging a mounting member on a mask shell to mount the seal and shell together. Headstrap retention bracket having an indentation for wedgedly engaging a mask shell cylinder to removably mount headstraps to the shell, the indentation circumscribed by an outward wall. Triangular mask seal of styrene-ethylene butylene-styrene copolymer modified with mineral oil.

17 Claims, 12 Drawing Sheets

MASK, MASK SHELL AND SEAL WITH IMPROVED MOUNTING, MASK SEAL, METHOD OF MASK MANUFACTURE AND MASK WITH REDUCED EXHALATION NOISE

BACKGROUND OF THE INVENTION

This invention relates generally to masks for supplying breathable gas to a person, and more particularly, relates to a nasal CPAP (Continuous Positive Airway Pressure) mask particularly useful for supplying pressurized breathing gas, such as oxygen, to a person in the treatment of obstructive sleep apnea.

The prior art is replete with masks which are of many different sizes, structures and for use in many different applications. Many different full face masks covering both the nose and the mouth are known to the art, and many different nasal masks covering only the nose are known to the art. A typical mask may include a shell of relatively hard or stiff material and a seal mounted to the shell and for conforming to the contours of a person's face, surrounding the nose and/or mouth, and for engaging such contours in an air-tight or sealing engagement. Such shell and seal may be made of numerous materials known to the art and also known to the art are numerous methods and structures for mounting the seal to the shell.

As is further known to the art, such masks typically include head gear comprising a plurality of headstraps which encircle the person's head and/or neck and which are adjustable to individualize the tension applied to the mask thereby individualizing the amount of force applied to the seal so that the seal will sealingly engage different contours of the faces of different people.

As is further known, the shells of such prior art masks are provided with venting means, such as a hole or plurality of holes, for preventing the accumulation of carbon dioxide in the shell and for providing for the exiting of the person's exhaled breath. Such prior art venting can produce a noisy or turbulent air flow or jet of air which can impinge annoyingly on the mask wearer or onto nearby persons such as a sleep partner.

Accordingly, it is believed that there is a need in the art for a mask having improved venting which reduces the noise level of the vented air and which directs the vented air away from the mask wearer thereby reducing discomfort to the mask wearer and annoyance to adjacent people such as a sleep partner.

Referring more particularly to the above-noted obstructive sleep apnea treatment, typically, in the night time treatment of obstructive sleep apnea, a nasal mask is placed over a person's nose and forced into sealing engagement with the contours of the patient's face surrounding the nose by adjusting and tightening the above-noted headstraps. The mask is connected to a ventilator which supplies breathing gas to the patient for the night time obstructive sleep apnea treatment. Typically, the adjustable headstraps are mounted fixedly to the mask which requires the headstraps to be loosened or removed to free the person from the mask for movement during the night time such as going to the bathroom. Upon return and recommencement of the obstructive sleep apnea treatment, the mask must again be placed into sealing engagement with the face and the headstraps again readjusted or retightened. This loosening and retightening of the headstraps is known to be quite annoying.

Further, the mask, particularly the seal, must be cleaned and since, as noted, the mask is typically mounted fixedly to the headstraps, this makes cleaning more difficult than is desirable. Further, the cleaning of a mask or seal mounted fixedly to the headstraps can cause the headstraps to become wet and possibly suffer shrinkage or at least some structural or functional impairment.

Accordingly, it is believed there is a need in the art for a new and improved mask mounted removably to the adjustable headstraps which permits the mask to be removed from the headstraps during the night time, freeing the person from the mask and ventilator and permitting the person to move about while the headstraps remain on the person's head, tightened and still individually adjusted to the patient's head. It is also believed there is a need in the art for such removable mask and headstrap combination which permits the mask and seal to be cleaned separately and apart from the headstraps.

Referring again to the prior art mask seals, some prior art mask seals are comprised of thermoset silicone, closed-cell foams, molded silicone and some include a soft material interposed between two thin plastic films and which are mounted to the mask shell by different mounting techniques. These prior art seal structures are generally known to be costly to manufacture.

Accordingly, it is further believed that there is a need in the art for a new and improved mask seal which may be manufactured cost effectively and for a new and improved structure for mounting the seal to the shell.

SUMMARY OF THE INVENTION

Mask seal having an embedded mounting member for engaging a mounting member on a mask shell to mount the seal and shell together. Headstrap retention bracket having an indentation for wedgedly engaging a mask shell cylinder to removably mount headstraps to the shell, the indentation circumscribed by an outward wall. Triangular mask seal of styrene-ethylene butylene-styrene copolymer modified with mineral oil.

DETAILED DESCRIPTION OF THE INVENTION

An embodiment of the mask of the present invention is shown in the drawings and indicated by general numerical designation 10. It will be understood that the mask 10 is dimensioned to be a nasal mask particularly useful as a nasal CPAP mask, but it will be still further understood that the mask of the present invention also may be embodied as other masks such as, for example and not by way of limitation, a full face mask.

Figure 1:
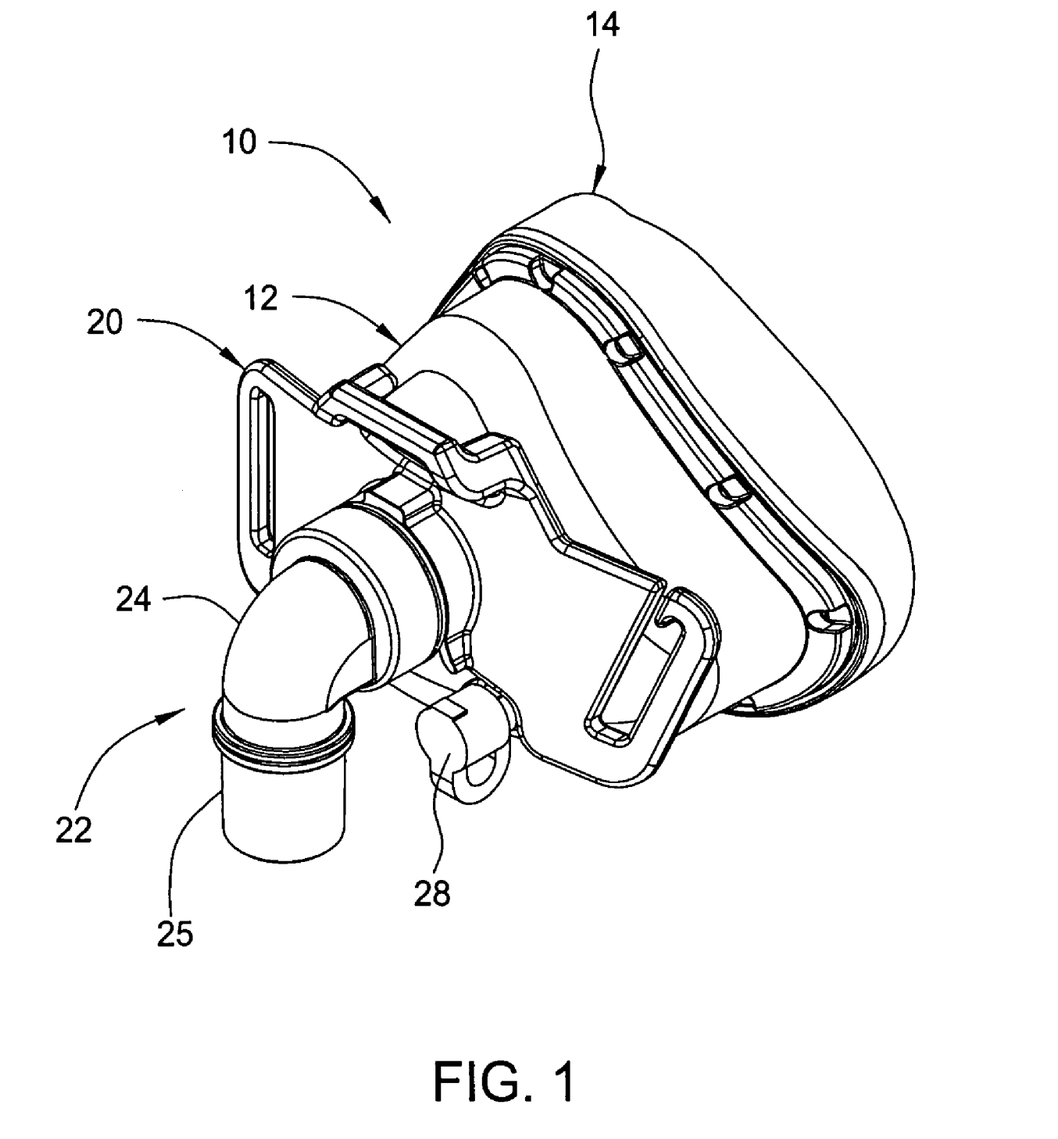
FIG. 1 is a perspective view of a mask embodying the present invention.
Figure 2A:
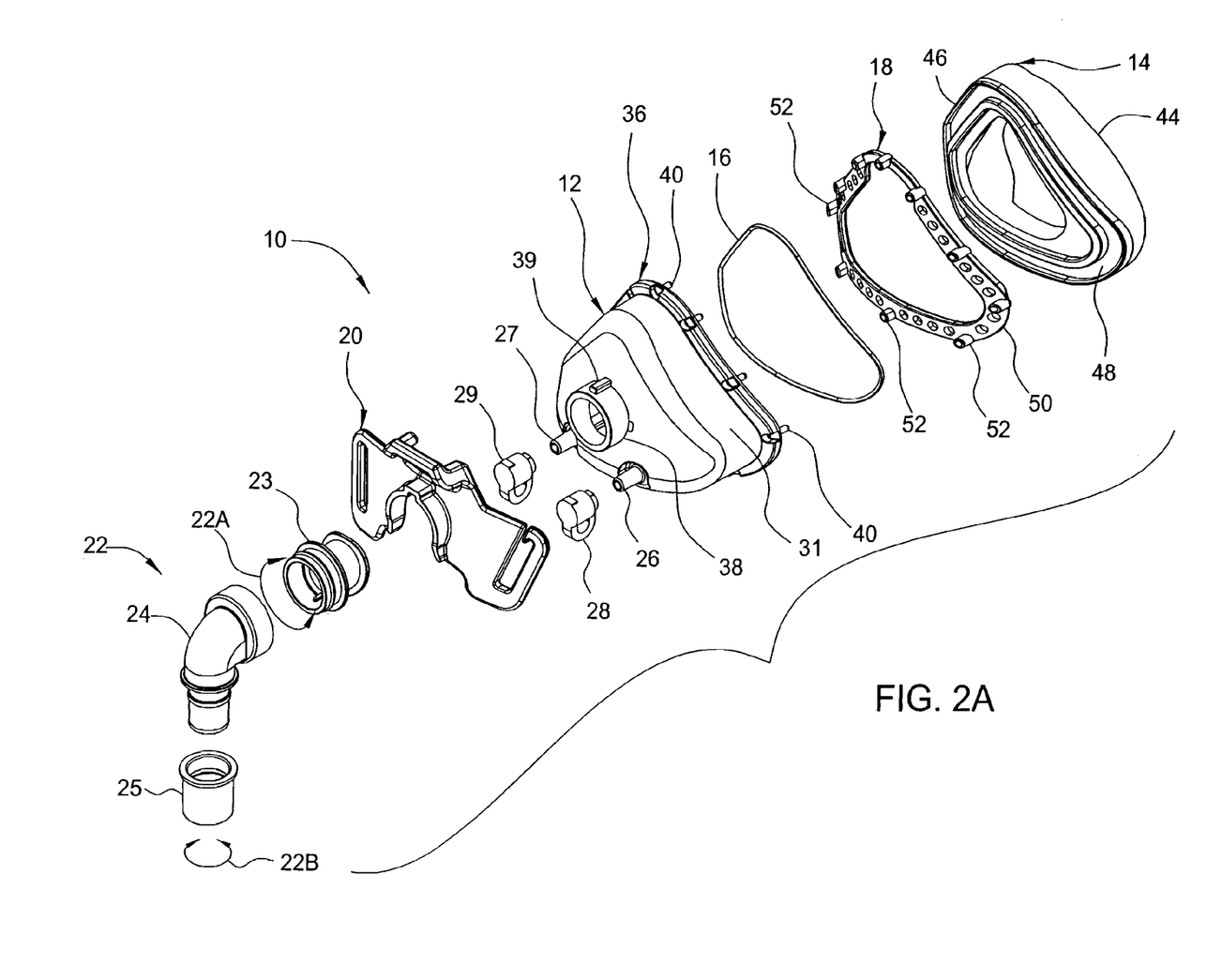
FIG. 2A is an exploded view taken generally from the left to the right showing the elements comprising the mask shell and seal of the present invention.
Figure 2B:
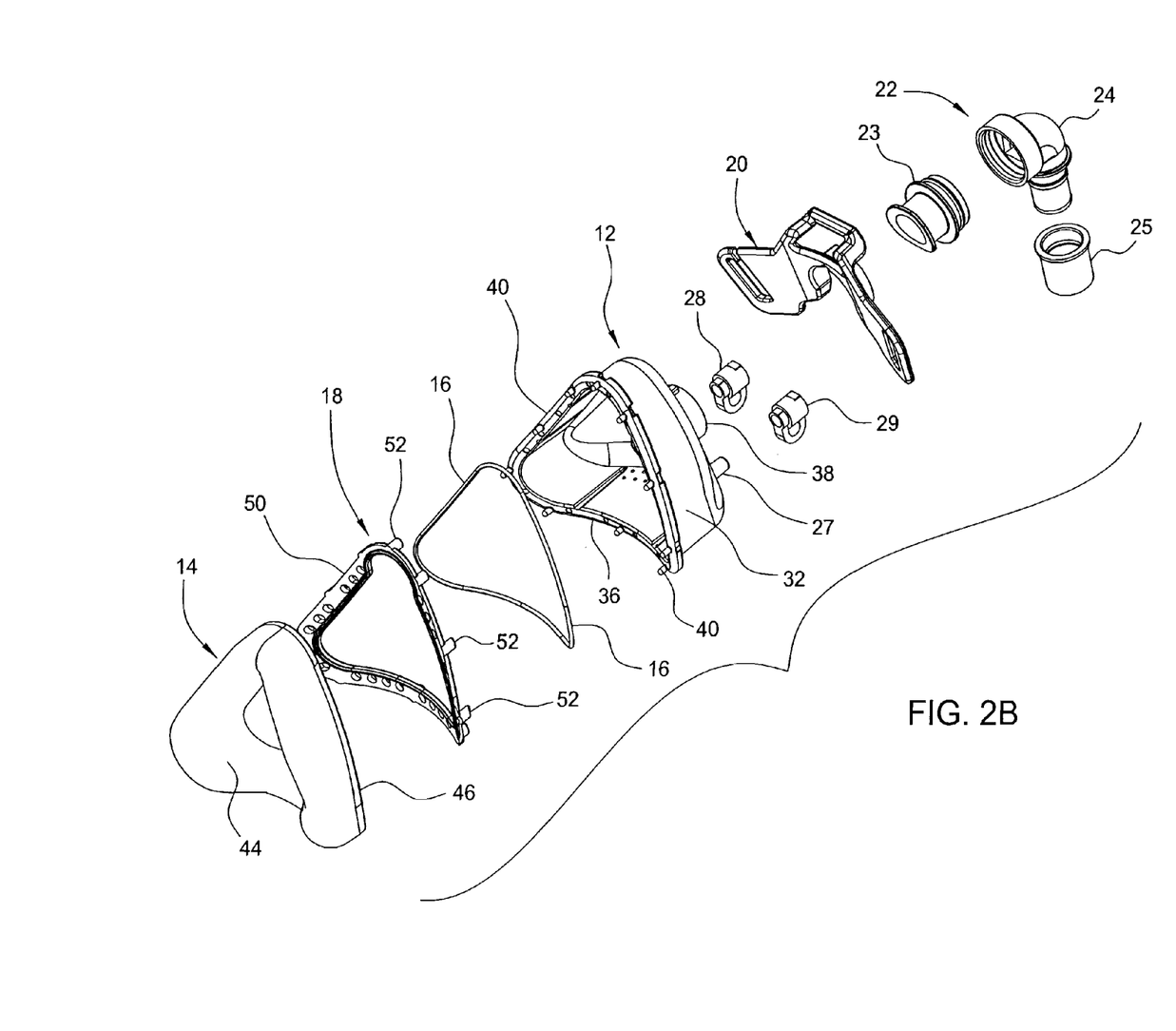
FIG. 2B is an exploded view substantially the reverse of FIG. 2A.

The mask 10, referring particularly to FIGS. 1 and 2A-2D, includes a mask shell indicated by general numerical designation 12, a mask seal indicated by general numerical designation 14, a hollow generally triangular malleable member 16, a hollow generally triangular seal mounting member indicated by general numerical designation 18, a head strap retention bracket indicated by general numerical designation 20, and a dual swivel indicated by general numerical designation 22 and of the type known to the art for providing swiveling in two directions as indicated by the double headed arrows 22A and 22B in FIG. 2A. The dual swivel 22 includes hollow conduit swivel members 23, 24 and 25 for being connected by a suitable gas supply hose to a suitable gas supply such as a ventilator or other positive airway pressure device (not shown) for supplying pressurized breathing gas to a wearer of the mask 10 during obstructive sleep apnea treatment. The mask shell 12, FIG. 2A, may be provided with two hollow cylindrical port members 26 and 27 in fluid communication with the interior of the shell and the mask may further include two removable port cap members 28 and 29 for opening and closing the port members 26 and 27. The port member 26 may be used, for example, to measure the pressure inside the mask and the port member 27 may be used to provide supplemental breathing gas, such as supplemental oxygen, to the mask and thereby to a wearer of the mask.

Figure 3:
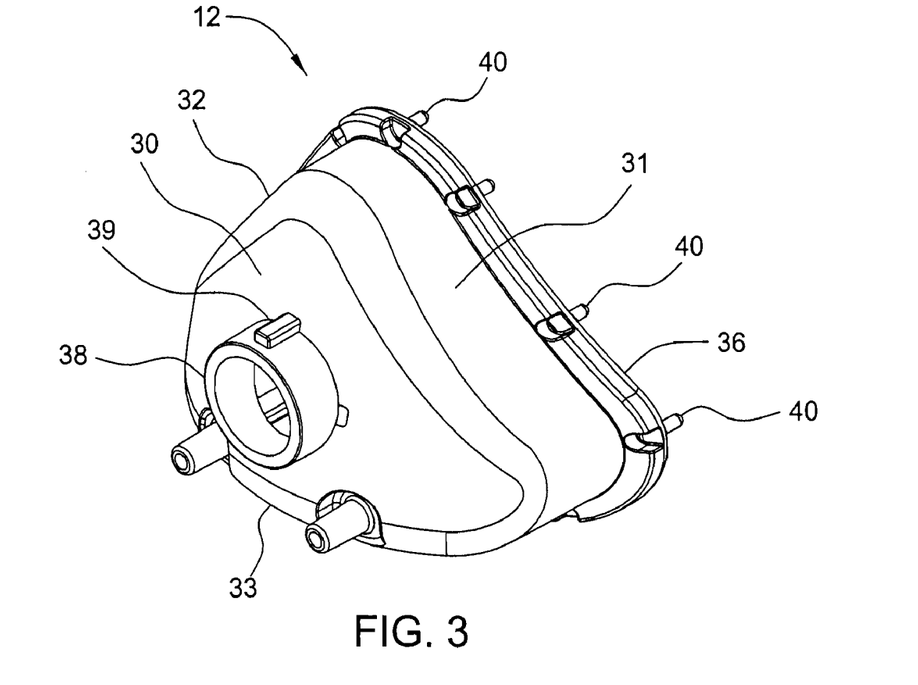
FIG. 3 is a front perspective view of the mask shell of the present invention.
Figure 4:
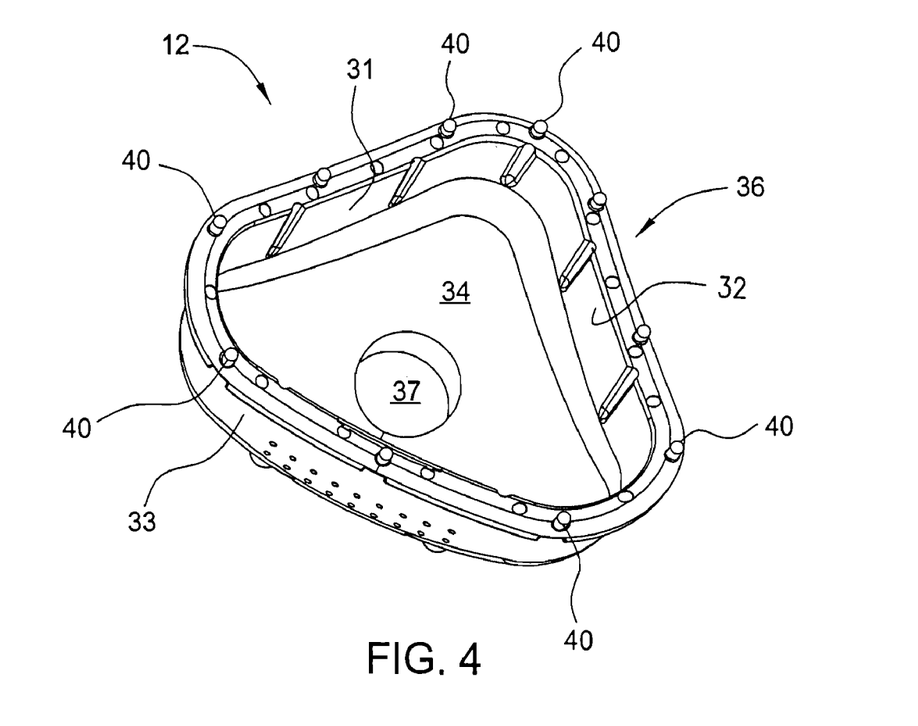
FIG. 4 is generally the reverse of FIG. 3 showing the interior of the mask shell.
Figure 5:
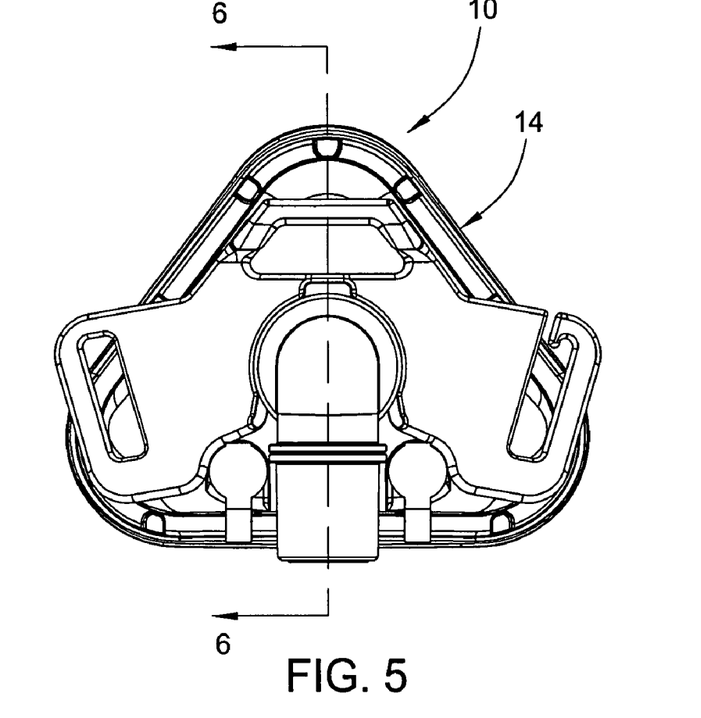
FIG. 5 is a front elevational view of the mask of the present invention.
Figure 6:
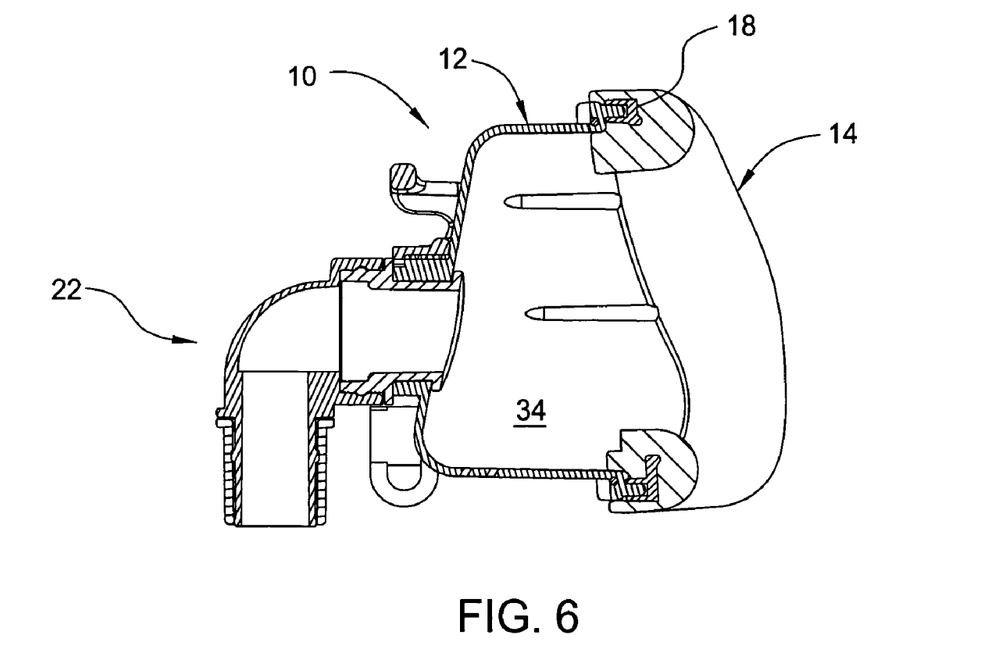
FIG. 6 is a cross-sectional view taken generally along the line 6-6 in FIG. 5 and in the direction of the arrows.

The mask shell 12, referring particularly to FIGS. 3 and 4, includes a top or an apex portion 30 and triangular walls 31, 32 and 33. The apex portion 30 and the triangular walls 31, 32 and 33 cooperatively provide the shell 12 with a generally triangular hollow interior 34 and the triangular walls 31, 32 and 33 terminate in, or provide the shell with, an outer shell periphery or peripheral portion indicated by general numerical designation 36. As may be best seen in FIG. 3, the shell apex portion 30 is provided with a circular opening 37 circumscribed by, as may be best seen in FIG. 3, an outwardly extending hollow cylindrical wall 38 provided with an outwardly extending rectangular radial ridge 39. The shell outer peripheral portion 36 is provided, as shown in FIGS. 3 and 4, with a plurality of outwardly extending solid generally cylindrical pins or connecting pins 40.

The mask shell 12 may be made from a suitable plastic, such as for example polyurethane, and made by suitable injection molding. It will be further understood that the hollow generally triangular malleable member 16 may be injection molded into the shell outer peripheral portion 36 by suitable injection molding techniques known to the art. The malleable member 16 in the preferred embodiment was a 0.304 stainless steel wire fully annealed at finish and having a diameter of about 0.052 inch.

Figure 2C:
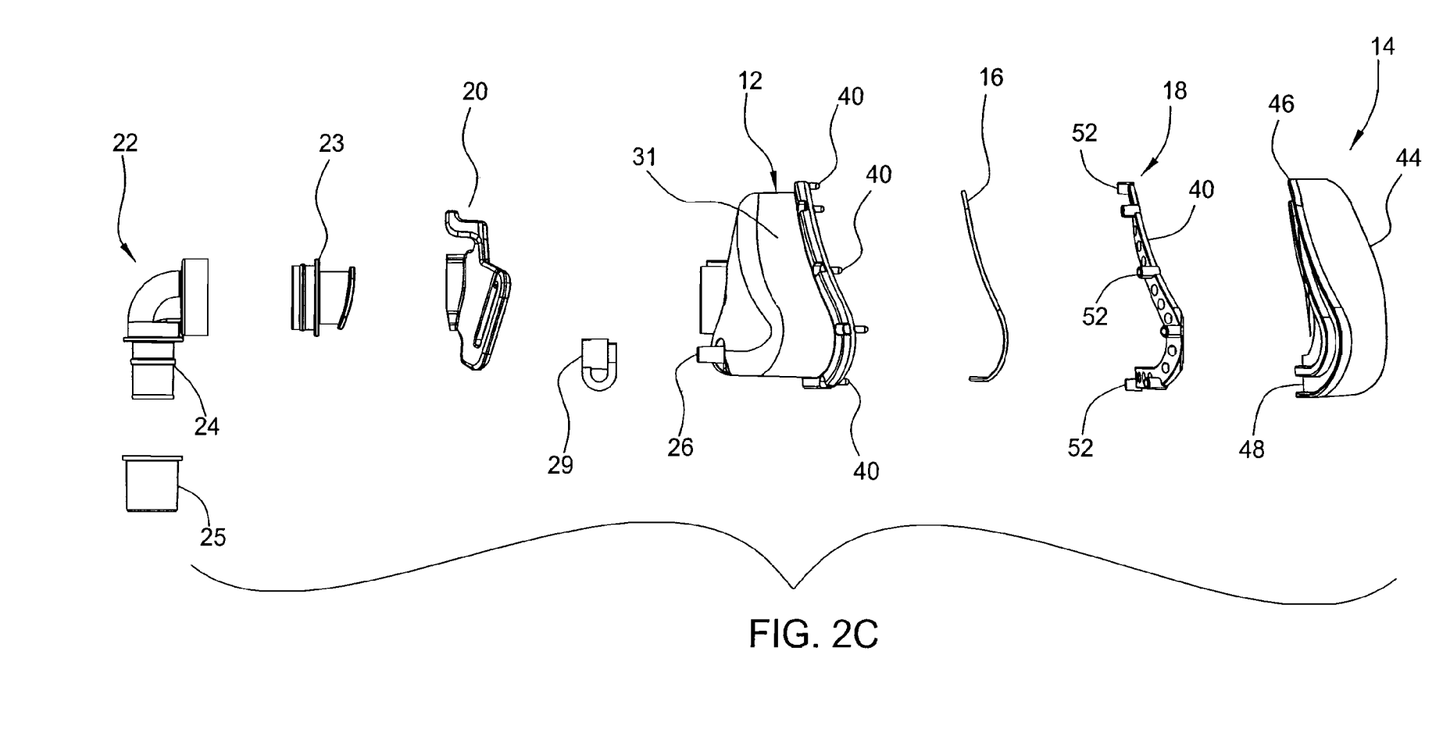
FIG. 2C is a side view of the mask elements shown in FIG. 2A.
Figure 2D:
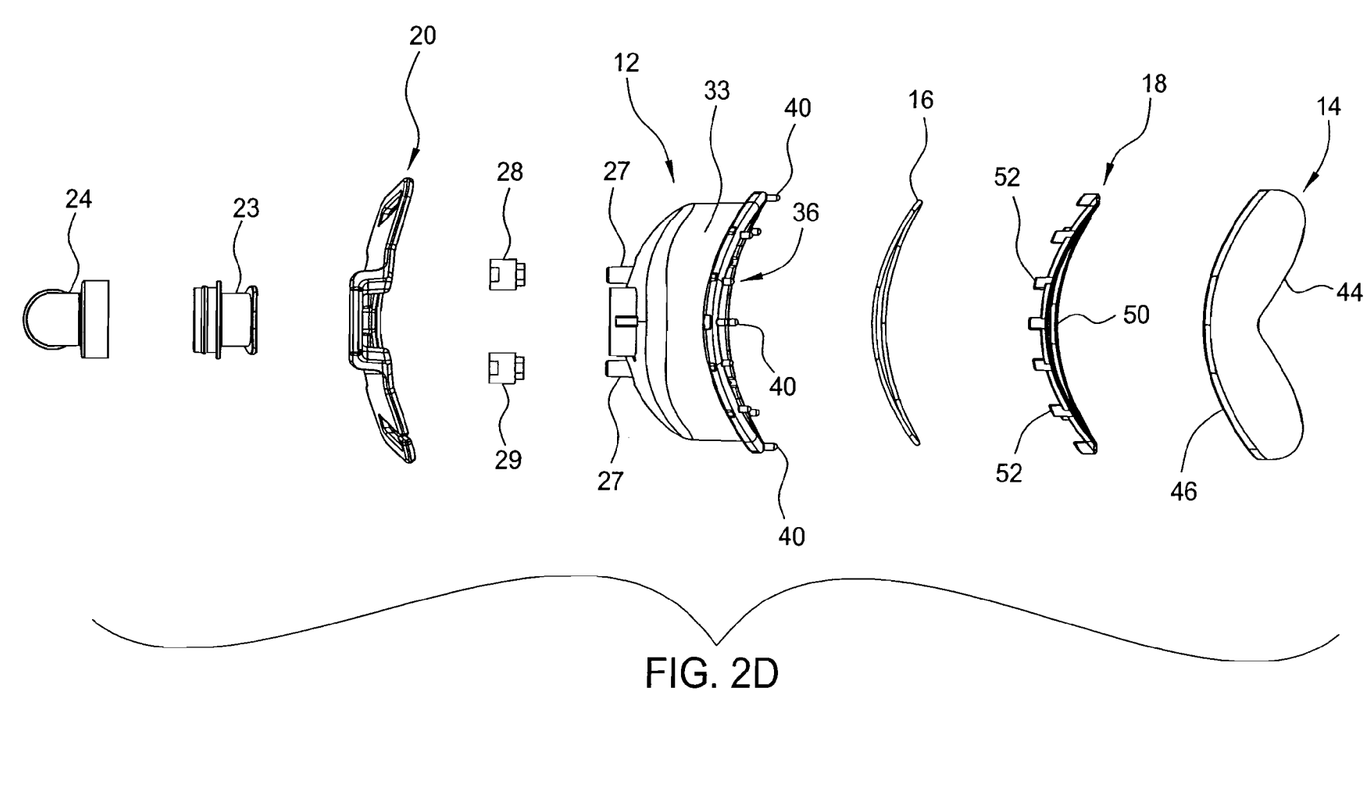
FIG. 2D is a top view of the mask element shown in FIG. 2A.
Figure 7:
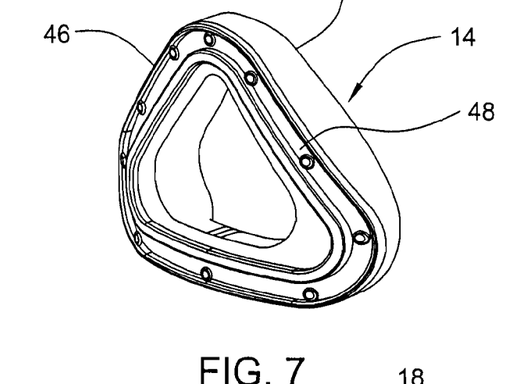
FIG. 7 is a perspective view of the mask seal of the present invention.
Figure 8:
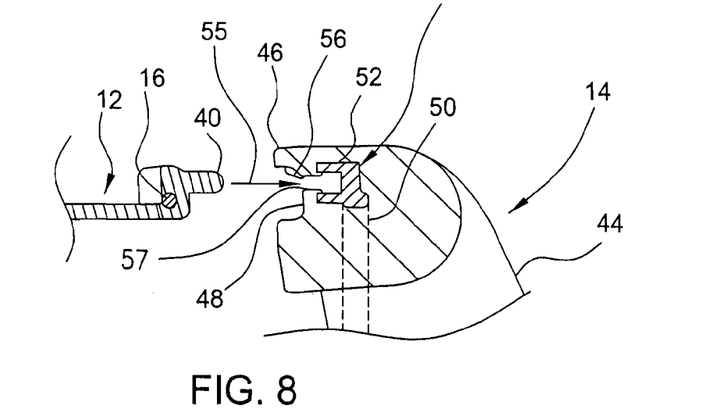
FIG. 8 is a diagrammatical illustration of the mounting of the mask seal to the mask shell of the present invention.

The seal 14, FIGS. 2A-2D, and 7-9, may be made of a suitable soft resilient material sufficiently soft to conform to the contours of a person's face surrounding the mask wearer's nose and sufficiently resilient to return to its original, or at least substantially its original, shape upon removal from the person's face. In the preferred embodiment, the seal 12 was made of a body of material comprising styrene-ethylene butylene-styrene copolymer modified with a mineral oil. Such material may also contain antioxidants and Vitamin E. Such material is available from California Medical Innovations, 873 E. Arrow Highway, Pamona, California 91767 and available under the name Dermasol. California Medical Innovations states that such material is a thermoplastic elastomer which has a durometer of 15-20 on the Shore 00 scale. It has been found that when such material is injection molded it has a durometer of about 63.6 on the Shore 000 scale. As shown in FIGS. 2A-2D, the seal 14 includes peripheral portions 44 and 46 with the peripheral portion 44 being provided with a contour to enhance sealing engagement with portions or contours of a person's face surrounding the nose and the peripheral portion 46, note particularly FIGS. 2A and 2C, and FIG. 7, is provided with a generally triangular indentation 48 complementary in shape to and for receiving the generally triangular shell peripheral portion 36 (FIGS. 3 and 4). The seal mounting member 18, note particularly FIGS. 2A and 2B, includes a hollow generally triangular frame 50 provided with a plurality of outwardly extending bosses 52. The seal mounting member 18 is molded into the seal periphery or peripheral portion 46 using injection molding techniques known to the art and is thereby embedded in the seal peripheral portion 46 as may be best understood from FIGS. 8 and 9. As will be further understood from FIG. 8, the mask seal 14 is mounted to the mask shell 12 by inserting, or forcing, the mask shell connecting pins 40 into the mask seal bosses 52 as indicated by the arrow 55 in FIG. 8. It will be understood that the shell connecting pins 40 and the seal bosses 52 are suitably dimensioned for an interference fit so as to mount the seal 14 fixedly to the shell 12. Such mounting is illustrated in detail in FIG. 9. Referring again to FIG. 8, it will be understood that the representative embedded seal boss 52 is slightly recessed behind the seal indentation 48 whereby the seal peripheral portions 56 and 57 will compress upon the pins 40 being inserted into the bosses 52 and act or function as a gasket to assure an air tight seal between the seal 14 and shell 12.

Figure 9:
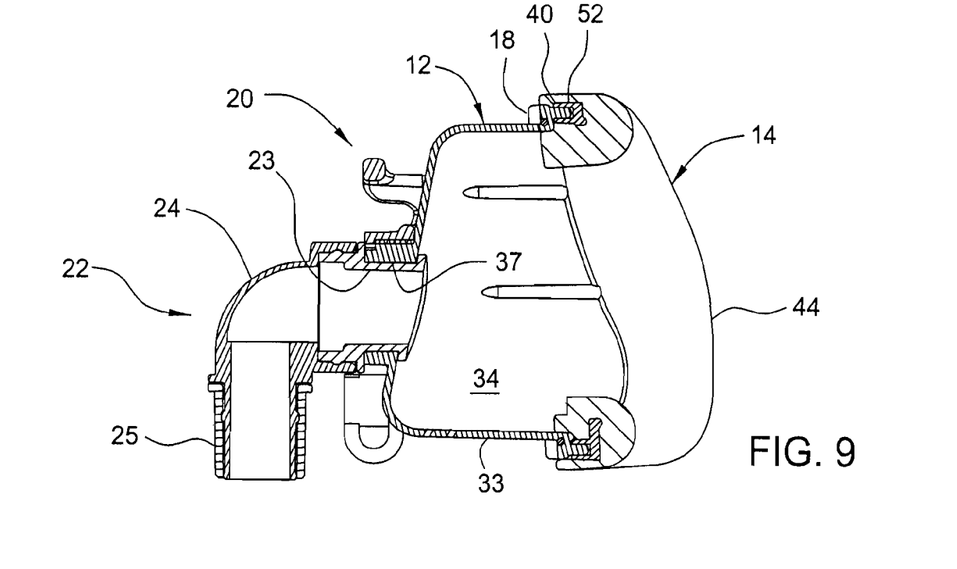
FIG. 9 is the same as FIG. 6 but showing in detail the mounting of the mask seal to the mask shell of the present invention and further illustrating in detail the mounting of the dual swivel members to the mask shell of the present invention.

As will be understood from FIG. 9, the dual swivel member 23 is mounted into the circular opening 37 (FIG. 4) formed in the apex shell portion 30 and the swivel members 24 and 25 are thereafter suitably mounted to each other, in the manner known to the art, to provide the above-described dual swiveling indicated by the double headed arrows 22A and 22B in FIG. 2A.

Figure 10:
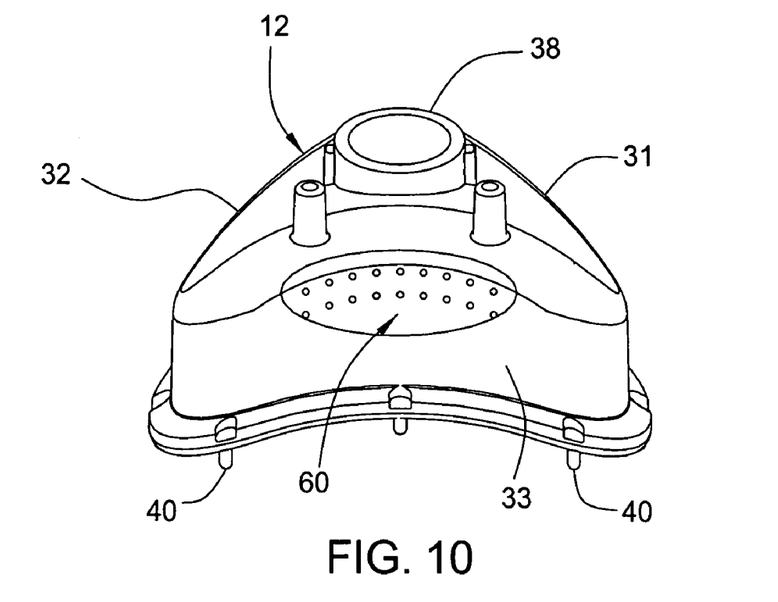
FIG. 10 is a perspective view taken generally from the bottom of the mask shell of the present invention and illustrating the vent holes of the present invention.
Figure 11:
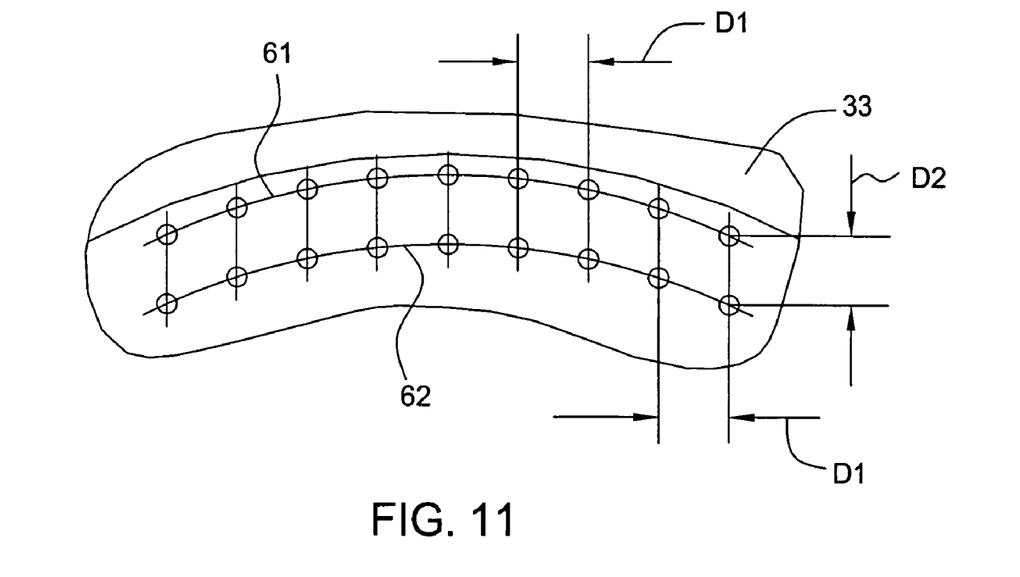
FIG. 11 is an enlarged view of the encircled portion of FIG. 10.

The mask and mask vent holes of the present invention are illustrated in FIGS. 10-13. The vent holes are exit vent holes and are for venting the exhaled breath of a wearer of the mask 10. As shown in FIGS. 10 and 11, the vent holes comprise a plurality of vent holes which are disposed in a curved array of vent holes including, in the preferred embodiment, two curved rows of vent holes; the plurality or curved array of vent holes are indicated by general numerical designation 60 in FIGS. 10 and 11, and the two rows of curved vent holes are indicated by numerical designations 61 and 62 in FIG. 11. It will be understood from FIG. 11 that the distance D1 between the vent holes in each row is equal to, or at least substantially equal to, the distance D2 between opposed vent holes or the vent holes in each curved row that are opposed to each other. The vent holes have a diameter, and it will be further understood from FIG. 11 that the distances D1 and D2 are equal to at least three times the diameter of the vent holes. In the preferred embodiment, the vent holes had a diameter of 0.040 inch and the distances D1 and D2 were 0.140 inch. It has been found that such vent hole diameter and vent hole spacings create a pattern of discrete laminar flow jets such that the flow exiting one vent hole does not generate turbulence in the flow from adjacent vent holes. This reduces the noise level generally associated with a person's exhaled breath exiting mask vent holes and such noise reduction reduces the annoyance to the wearer of the mask, and to a sleep partner, which generally arises from a patient's exhaled breath exiting mask vent holes known to the prior art.

Figure 12:
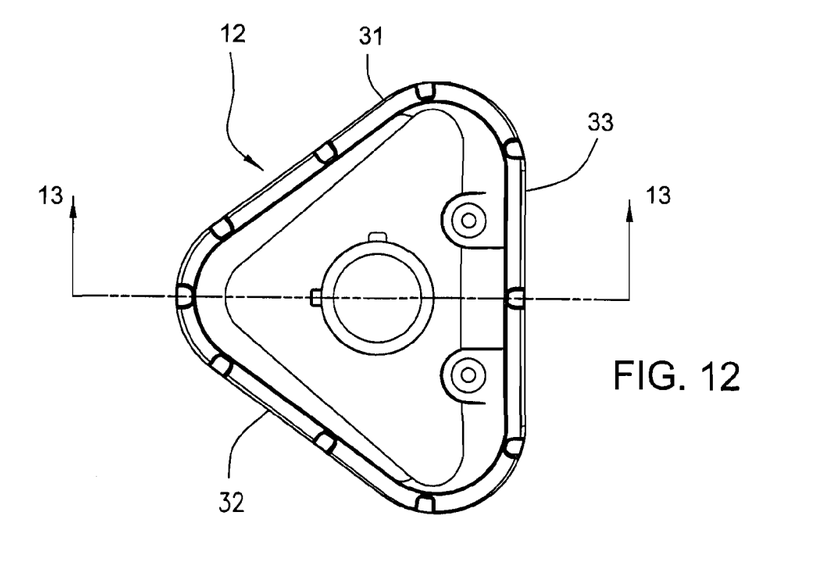
FIG. 12 is a front view of the mask shell of the present invention.
Figure 13:
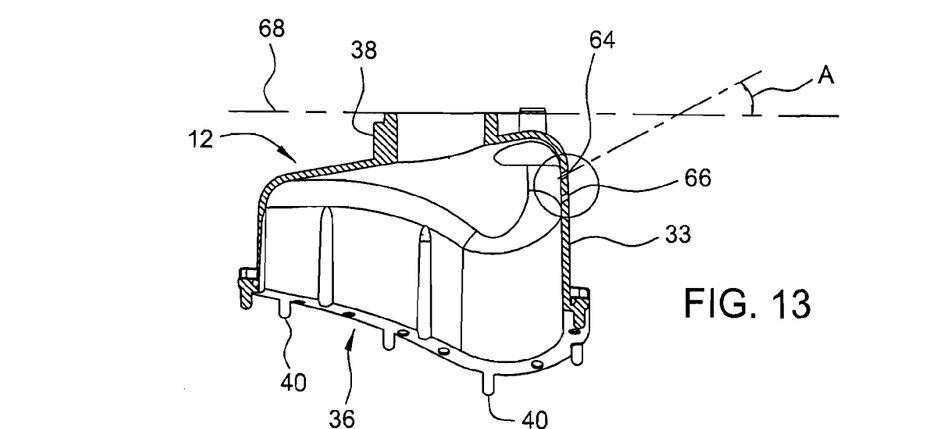
FIG. 13 is a cross-sectional view taken generally along the line 13-13 in FIG. 12 and in the direction of the arrows.
Figure 13A:
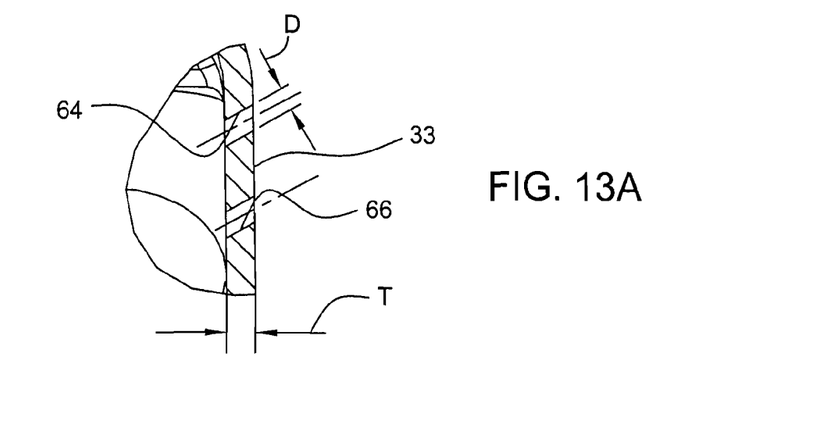
FIG. 13A is an enlarged view of the encircled portion of FIG. 13.

The angular disposition of the cylindrical vent holes of the present invention is illustrated in FIGS. 12-13A. Representative vent holes 64 and 66 are shown in FIGS. 13 and 13A. As will be understood from FIG. 13, the outwardly extending hollow cylindrical wall 38 of the mask shell 12 terminates in a plane 68, and as will be further understood from FIG. 13 the vent holes, note representative vent hole 64, are disposed at an acute exit angle A with respect to the plane 68; in the preferred embodiment the angle A was 30°. As will be further understood from FIG. 13A, the wall 33 in which the vent holes are formed has a thickness T and the vent holes have a diameter D which is less than the thickness T. In the preferred embodiment, the mask wall 33 had a thickness of 0.050 inch and the vent holes had a diameter D of 0.040 inch. It has been found that such angular disposition of the vent holes in the mask shell wall 33 causes the patient's exhaled breath to exit in a flow stream which is substantially parallel to the body of the wearer of the mask 10. This permits the person's exhaled breath to escape the mask without causing discomfort to the wearer of the mask or to a sleep partner onto which the escaped exhaled breath may be flowing or escaping.

Figure 14:
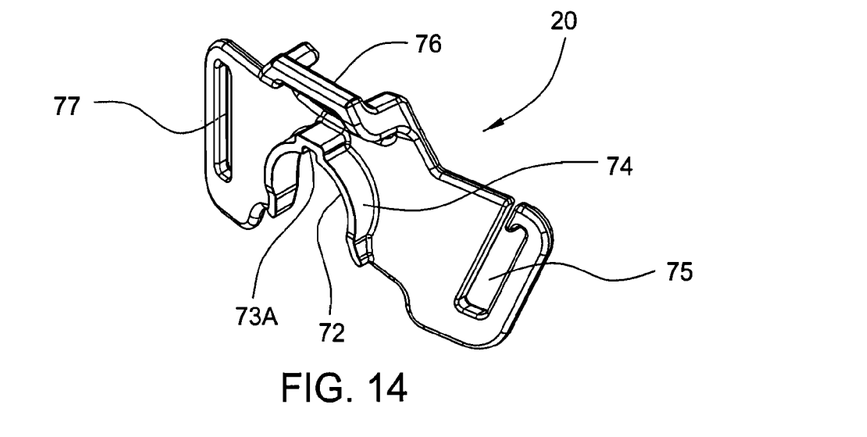
FIG. 14 is a separate perspective view of the headstrap retention bracket of the present invention.
Figure 15:
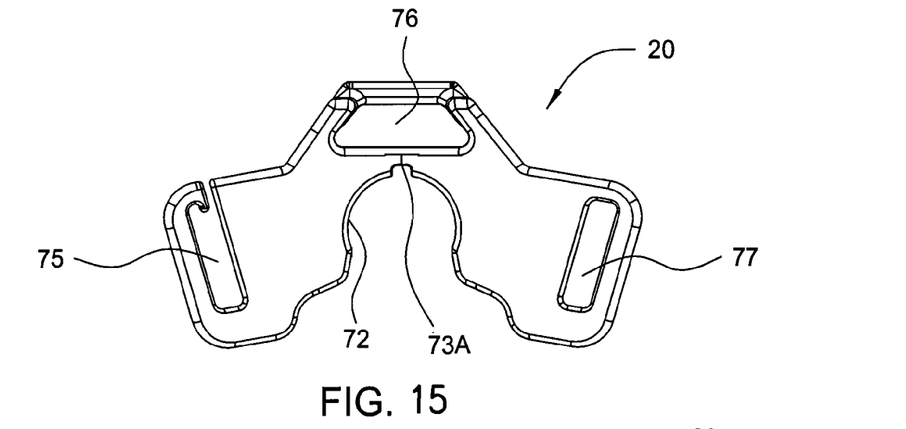
FIG. 15 is a rear elevational view of the headstrap retention bracket of the present invention.
Figure 16:
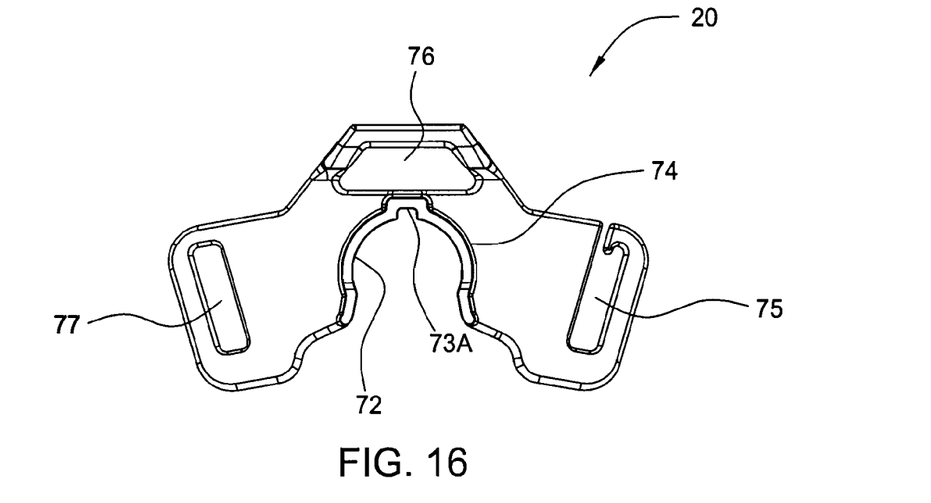
FIG. 16 is a front elevational view of the headstrap retention bracket of the present invention.

The removable mounting of the mask seal 14 and shell 12 of the mask 10 of the present invention to the headstraps for fastening the mask to a wearer's face is provided, in part, by the headstrap retention bracket 20 shown in separate detail in FIGS. 14-16. The headstrap retention bracket 20 is provided with a generally semi-circular indentation 72, FIG. 15, which is provided generally centrally with an outwardly extending rectangular indentation 73. The indentations 72 and 73, FIGS. 14 and 16, are circumscribed by an outwardly extending generally semi-circular wall or member 74 including a radially outwardly extending portion providing a radially inwardly extending recess 73A. The wall 74 is complementary in shape to and for receiving portions of the shell hollow cylindrical wall 38 in a wedged or friction engagement with the radial ridge being received in the radial recess 73A. The headstrap retention member 20, FIGS. 14-16, is provided with three openings 75, 76 and 77 for respectively receiving headstraps 78, 79 and 80 as shown in FIGS. 17 and 18.

Figure 17:
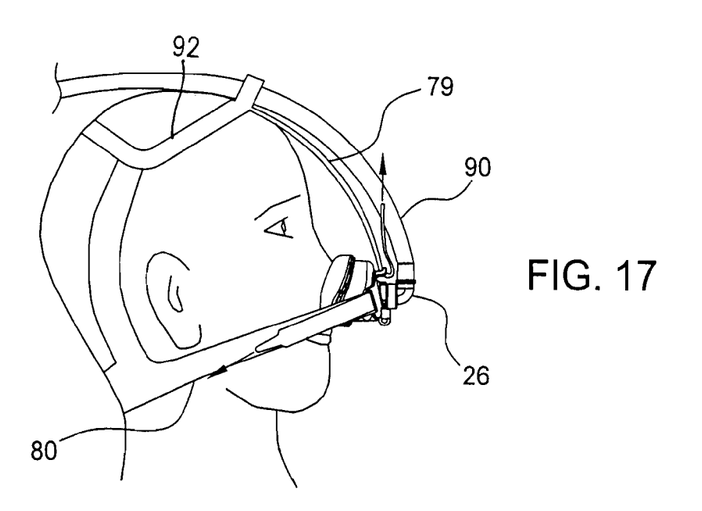
FIG. 17 is an illustration of the mask of the present invention attached by headstraps to the portions of a person's face surrounding the nose.

The mask 10 of the present invention may include such headstraps and is illustrated as being attached to a person's face in FIG. 17 as a nasal CPAP mask for the treatment of obstructive sleep apnea treatment. A corrugated gas supply hose 90 is attached to the dual swivel hollow conduit member 26 (FIG. 1) and is inserted through a headstrap member 92, FIG. 17, and is further connected to a ventilator (not shown), in the manner known to the art, for supplying pressurized breathing gas to a person for the above-noted night time sleep apnea treatment.

Figure 18:
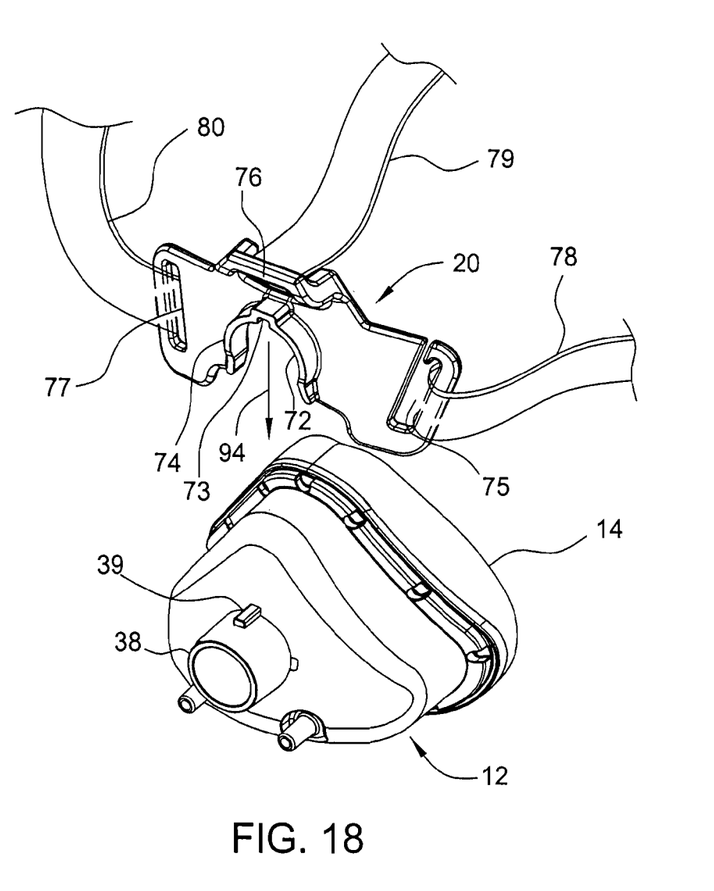
FIG. 18 is an illustration of the removable mounting of the mask shell and seal of the present invention to a headstrap retention bracket of the present invention and thereby to the headstraps of the mask of the present invention.

The removable mounting of the mask shell 12 and seal 14 to the headstraps 78-80 is illustrated diagrammatically in FIG. 18. The headstraps are inserted through the loops or holes formed in the headstrap retention bracket 20, as illustrated diagrammatically in FIG. 18, and the headstrap retention bracket 20, as indicated by the downwardly extending arrow 94 in FIG. 18 is forced downwardly, with manual force applied by the person to wear the mask, to force the generally semi-circular wall 74 of the headstrap retention bracket 20 into wedged or interference friction engagement with the portions of hollow cylindrical wall 38 provided on the mask shell 12 and with the mask shell outwardly extending rectangular radial ridge 39 being received within the inwardly extending rectangular recess 73 formed in the wall 74 of the head retention bracket 20. The receipt of the ridge 39 in the recess 73A orients the head retention bracket 20 to the shell 12 and seal 14 and thereby orients the headstraps to the mask shell and seal. Also, this mounts the mask shell 12 and seal 14 removably to the headstrap retention bracket 20, and thereby removably to the headstraps 78-80, which permits the mask shell 12 and seal to be removed from the headstrap retention bracket, and thereby from the headstraps, with the use of manual force from the mask wearer.

Upon the mask shell 12 and seal 14 being mounted to the headstrap retention bracket 20 and the headstraps 78-80, the headstraps may be placed over and around portions of the person's head as shown in FIG. 17 and manual force from the mask wearer is used to apply tension to the adjustable headstrap members, as indicated by the arrows in FIG. 17, to adjust the tension supplied to the mask and to adjust the amount of force with which the mask seal 14 is forced into air tight sealing engagement with the portions of the mask wearer's face surrounding the nose. The malleable member 16, embedded in the outer peripheral portion of the mask shell 12, particularly FIGS. 8 and 9, may be deformed to further individualize or customize the fitting of the mask seal 14 to the portions or contours of the mask wearer's face surrounding the nose.

Should, for example, the mask wearer undergoing the noted obstructive sleep apnea treatment need to get up and move about, such as to go to the bathroom, the previously adjusted headstraps need not be removed from the person's face but instead, the previously adjusted headstraps may remain adjusted and fastened to the person's head, and the mask shell 12 and seal 14 may be removed from the headstrap retention bracket while the headstraps remain attached to the person's head. Such removal is accomplished by the use of manual force from the mask wearer with the mask shell 12 and seal 14 being pulled downwardly, opposite the direction of the arrow 94 in FIG. 18, to disengage or unwedge the mask shell cylindrical wall 38 from the semi-cylindrical wall 74 of the headstrap retention bracket 20. The gas supply hose 90, FIG. 19, is then removed from the headstrap member 92 and the person is now free from the mask shell 12, seal 14 and the gas supply hose 90. The person may move about freely while the headstraps remain previously individualized and attached to the person's head. Upon the person returning to resume the sleep apnea treatment, the mask shell 12 and seal 14 are again mounted to the headstrap retention bracket 20 as described above and illustrated in FIG. 18.

It will be understood by those skilled in the art that many variations and modifications may be made in the present invention without departing from the spirit and the scope thereof.

What is claimed is:

1. Mask, comprising,
  a generally triangular shell including an apex portion and triangular walls providing an interior and including a shell outer peripheral portion, said apex portion provided with a circular opening circumscribed by an outwardly extending hollow cylindrical member for supplying gas to said mask, said shell outer peripheral portion provided with first mounting means;
  a seal including a seal outer peripheral portion;
  second mounting means embedded wholly within said seal outer peripheral portion except for a portion providing access to said first mounting means and for engaging said first mounting means to mount seal to said shell;
  one of said walls for being disposed beneath a person's nose and wherein said one wall is provided with a plurality of vent holes extending upwardly from said interior and angularly outwardly through said one wall;
  a malleable member mounted in said shell outer peripheral portion and for being deformed to deform said shell and thereby said seal to fit said seal to portions of a person's face;
  a plurality of adjustable headstraps for surrounding and being attached to a person's head; and
  a headstrap retention bracket mounted to said plurality of headstraps and provided with an inwardly extending generally semi-circular indentation generally complementary in shape to said cylindrical member and for permitting said headstrap retention bracket to wedgedly engage said cylindrical member to mount said shell and said seal removably to said plurality of headstraps.

2. The mask according to claim 1 wherein said first mounting means comprise a plurality of pins extending outwardly from said shell outer peripheral portion and wherein said second mounting means comprises a plurality of bosses extending outwardly to said seal outer peripheral portion and for wedgedly receiving said pins.

3. The mask according to claim 1 wherein said seal comprises a generally hollow triangular body comprising a styrene-ethylene butylene, styrene copolymer modified with a mineral oil.

4. The mask according to claim 1 wherein said seal comprises a generally hollow triangular body comprising a styrene-ethylene butylene-styrene copolymer modified with a mineral oil having a durometer of about 63.6 on the Shore 000 scale.

5. The mask according to claim 1 wherein said seal comprises a body of moldable material and wherein said second mounting means is embedded in said seal outer peripheral portion by being molded into said moldable material.

6. The mask according to claim 5 wherein said moldable material comprises a styrene-ethylene butylene-styrene copolymer modified with a mineral oil.

7. The mask according to claim 1 wherein said shell comprises a body of first moldable material, wherein said first mounting means comprise a plurality of pins extending outwardly from said shell outer peripheral portion, and wherein said seal comprises a body of second moldable material and wherein said second mounting means comprise a plurality of outwardly extending bosses for wedgedly receiving said pins.

8. The mask according to claim 7 Wherein said second mounting means comprise a hollow generally triangular frame embedded into said seal outer peripheral portion and provided with said plurality of bosses.

9. The mask according to claim 1 wherein said mask comprises a body of moldable material and wherein said malleable member is molded into said shell outer peripheral portion.

10. The mask according to claim 1 wherein said plurality of vent holes are disposed at an exit angle of approximately 30° with respect to said one wall.

11. The mask according to claim 1 wherein said one wall has a thickness and wherein said vent holes are cylindrical and have a diameter less than said thickness of said one wall.

12. The mask according to claim 1 wherein said hollow cylindrical member is provided with an outwardly extending radial ridge. wherein said generally semi-circular indentation is provided generally centrally with an outwardly extending radial indentation, wherein said semi-circular indentation and said radial indentations are circumscribed by an outwardly extending generally semi-cylindrical member including an inwardly extending portion providing a radial recess and wherein said generally semi-cylindrical indentation is for wedgedly engaging said cylindrical member with said radial recess receiving said radial ridge to orient said retention bracket with respect to said shell and to mount said shell and said seal removably to said plurality of headstraps.

13. The mask according to claim 1 wherein said seal outer peripheral portion is provided with a seal indentation complementary to and for receiving said shell outer peripheral portion to facilitate mounting of said seal to said shell.

14. The mask according to claim 1 wherein said plurality of vent holes comprise an array of vent holes including at least two opposed curved rows of vent holes.

15. The mask according to claim 14 wherein the distance between the vent holes in each row is substantially the same as the distance between opposed bent holes.

16. The mask according to claim 15 wherein said vent holes have a diameter and wherein said distances between vent holes are at least three times said diameter.

17. A mask, comprising:
  a shell and a seal mounted to said shell, said shell provided with an outwardly extending hollow cylinder for supplying gas and in fluid communication with said shell;
  a plurality of headstraps;
  a headstrap retention bracket mounted to said headstraps and provided with a generally semi-circular indentation permitting said, bracket to wedgedly engage said cylinder and mount said shell and said seal removably to said plurality of headstraps;

said cylindrical member provided with an outwardly extending radial ridge;

said generally semi-circular indentation is provided generally centrally with an outwardly extending radial indentation;

said generally semi-circular indentation and said outwardly extending radial indentation circumscribed by an outwardly extending generally semi-circular member including a portion providing an outwardly radial extending recess; and said generally semi-circular member for wedgedly engaging portions of said cylindrical member with said radial recess receiving said radial ridge to orient said headstraps with respect to said shell and to said seal and to mount said shell and said seal removably to said plurality of headstraps.

\* \* \* \* \*